US012752081B2

(12) United States Patent
Avivi

(10) Patent No.: US 12,752,081 B2
(45) Date of Patent: Oct. 6, 2026

(54) STEERABLE MEDICAL DEVICE, HANDLE FOR A MEDICAL DEVICE, AND METHOD FOR OPERATING A MEDICAL DEVICE

(71) Applicant: Boston Scientific Medical Device Limited, Galway (IE)

(72) Inventor: Doran Avivi, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 705 days.

(21) Appl. No.: 18/296,660

(22) Filed: Apr. 6, 2023

(65) Prior Publication Data

US 2023/0248943 A1 Aug. 10, 2023

Related U.S. Application Data

(63) Continuation of application No. PCT/IB2021/057920, filed on Aug. 30, 2021.

(60) Provisional application No. 63/089,606, filed on Oct. 9, 2020.

(51) Int. Cl.
*A61M 25/01* (2006.01)
*A61B 17/00* (2006.01)

(52) U.S. Cl.
CPC ... *A61M 25/0136* (2013.01); *A61B 17/00234* (2013.01); *A61M 25/0147* (2013.01); *A61B 2017/00318* (2013.01)

(58) Field of Classification Search
CPC ........... A61M 25/0136; A61M 25/0147; B20L 7/00318
See application file for complete search history.

(56) References Cited

U.S. PATENT DOCUMENTS

| | | | |
|---|---|---|---|
| 5,456,664 A | 10/1995 | Heinzelman et al. | |
| 2012/0089125 A1* | 4/2012 | Scheibe ............ | A61M 25/0147 604/523 |
| 2014/0088553 A1 | 3/2014 | Hetherington | |

FOREIGN PATENT DOCUMENTS

| | | |
|---|---|---|
| EP | 566724 B1 | 5/1999 |
| WO | 2016118426 A1 | 7/2016 |

OTHER PUBLICATIONS

International Search Report for PCT Application No. PCT/IB2021/057920 mailed Dec. 3, 2021.

* cited by examiner

*Primary Examiner* — Laura A Bouchelle
(74) *Attorney, Agent, or Firm* — Nelson Mullins Riley & Scarborough LLP

(57) ABSTRACT

A steerable medical device includes an elongate tool and a handle mounted to the tool. The handle has a handle body and a knob that is rotatable with respect to the handle body. A first gear is housed within the handle and is associated with the knob, so that rotation of the knob drives rotation of the first gear. A slider is housed within the handle body and includes a rack engaged with the first gear, so that rotation of the first gear drives translation of the slider with respect to the handle body. At least one control wire is coupled to the tool, so that translation of the slider causes tensioning of the control wire, and tensioning of the control wire causes deflection of the tool.

9 Claims, 3 Drawing Sheets

STEERABLE MEDICAL DEVICE, HANDLE FOR A MEDICAL DEVICE, AND METHOD FOR OPERATING A MEDICAL DEVICE

CROSS-REFERENCE TO RELATED APPLICATIONS

This application is a continuation of and claims the benefit of International Application Number PCT/IB2021/057920, entitled "STEERABLE MEDICAL DEVICE, HANDLE FOR A MEDICAL DEVICE, AND METHOD FOR OPERATING A MEDICAL DEVICE," and filed Aug. 30, 2021, which claims the benefit of U.S. Provisional Application No. 63/089,606, entitled "STEERABLE MEDICAL DEVICE, HANDLE FOR A MEDICAL DEVICE, AND METHOD FOR OPERATING A MEDICAL DEVICE," and filed Oct. 9, 2020, which are hereby incorporated by reference in their entireties.

FIELD

This document relates to medical devices. More specifically, this document relates to steerable medical devices such as steerable sheaths, catheters, and introducers.

SUMMARY

The following summary is intended to introduce the reader to various aspects of the detailed description, but not to define or delimit any invention.

Steerable medical devices are disclosed. According to some aspects, a steerable medical device includes an elongate tool, and a handle mounted to the tool. The handle has a handle body and a knob that is rotatable with respect to the handle body. A first gear is housed within the handle and is associated with the knob. Rotation of the knob drives rotation of the first gear. A slider is housed within the handle body and includes a rack engaged with the first gear. Rotation of the first gear drives translation of the slider with respect to the handle body. At least one control wire is coupled to the slider and to the tool. Translation of the slider causes tensioning of the control wire, and tensioning of the control wire causes deflection of the tool.

In some examples, the handle extends along a handle axis, and the slider is translatable along the handle axis.

The knob can be rotatable about the handle axis, and the first gear can be a worm screw that is rotatable about the handle axis. Alternatively, the knob can be rotatable about an axis of rotation that is non-parallel to the handle axis, and the first gear can be a worm screw that is rotatable about the handle axis. The steerable medical device can further include at least one additional gear coupled between the knob and the worm screw.

The knob can be rotatable about the handle axis, and the first gear can be a pinion gear that is rotatable about an axis of rotation that is perpendicular to the handle axis. The steerable medical device can further include at least one additional gear coupled between the knob and the pinion gear. The steerable medical device can further include a pawl or latch configured to prevent movement of the slider when the control wire is under tension.

The tool can be a sheath, a catheter, or an introducer.

Handles for steerable medical devices are also disclosed. According to some aspects, a handle for a steerable medical device includes a handle body and a knob that is rotatable with respect to the handle body. A first gear is housed within the handle and is associated with the knob. Rotation of the knob drives rotation of the first gear. A slider is housed within the handle body and includes a rack engaged with the first gear. Rotation of the first gear drives translation of the slider with respect to the handle body. At least one control wire is coupled to the slider. Translation of the slider causes tensioning of the control wire.

In some examples, the handle extends along a handle axis, and the slider is translatable along the handle axis.

The knob can be rotatable about the handle axis, and the first gear can be a worm screw that is rotatable about the handle axis. Alternatively, the knob can be rotatable about an axis of rotation that is non-parallel to the handle axis, and the first gear can be a worm screw that is rotatable about the handle axis. The handle can further include at least one additional gear coupled between the knob and the worm screw.

The knob can be rotatable about the handle axis, and the first gear can be a pinion gear that is rotatable about an axis of rotation that is perpendicular to the handle axis. The handle can further include at least one additional gear coupled between the knob and the pinion gear. The handle can further include a pawl or latch configured to prevent movement of the slider when the control wire is under tension.

Methods for operating a medical device are also disclosed. According to some aspects, a method for operating a medical device includes: a. rotating a knob of a handle; b. transmitting rotation of the knob to a first gear associated with the knob; c. engaging the first gear with a rack of a slider to cause translation of the slider by rotation of the first gear; d. causing tensioning of a control wire by translation of the slider; and e. causing deflection of a tool by tensioning of the control wire.

In some examples, the first gear is a worm gear, step a. includes rotating the knob about a handle axis, and step b. includes rotating the worm gear about the handle axis.

In some examples, the first gear is a pinion gear, step a. includes rotating the knob about a handle axis, and step b. includes rotating the pinion gear about an axis of rotation that is perpendicular to the handle axis.

Rotation of the knob can be transmitted to the first gear via at least one additional gear.

The method can further include using a pawl or latch to prevent movement of the slider.

In some examples, the handle extends along a handle axis, the first gear is a worm gear, step a. comprises rotating the knob about an axis of rotation that is non-parallel to the handle axis, and step b. comprises rotating the worm gear about the handle axis.

BRIEF DESCRIPTION OF THE DRAWINGS

The accompanying drawings are for illustrating examples of articles, methods, and apparatuses of the present disclosure and are not intended to be limiting. In the drawings.

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are steerable medical devices that include a handle and a tool such as a sheath, a catheter, or an introducer. The handle can enable the user to manipulate or steer the tool in a desired direction. More specifically, the handle can include a knob that is rotatably coupled to a housing (also referred to as a 'body') of the handle. In operation, rotation of the knob can allow the user to steer or deflect the tool. Rotation of the knob can be converted into deflection of the tool via a gear (e.g. a worm screw or a pinion gear) coupled to the knob, a slider that includes a rack coupled to the gear, and one or more control wires, which can be coupled between the slider and the tool. Rotation of the knob can cause rotation of the gear, rotation of the gear can cause translation of the slider, and translation of the slider can cause tensioning of the control wire(s), which results in deflection of the tool. For simplicity, details of the control wire(s) and the connection between the control wire(s), the tool, and the slider are not disclosed herein. However, related sliders and control wires are disclosed in, for example, U.S. Pat. No. 10,661,057 (Davies et al.), which is incorporated herein by reference in its entirety. Furthermore, steerable medical devices including sliders and control wires are sold Baylis Medical Company, Inc. (Montreal, Canada) under the brand name SureFlex® Steerable Guiding Sheath.

Figure 1:
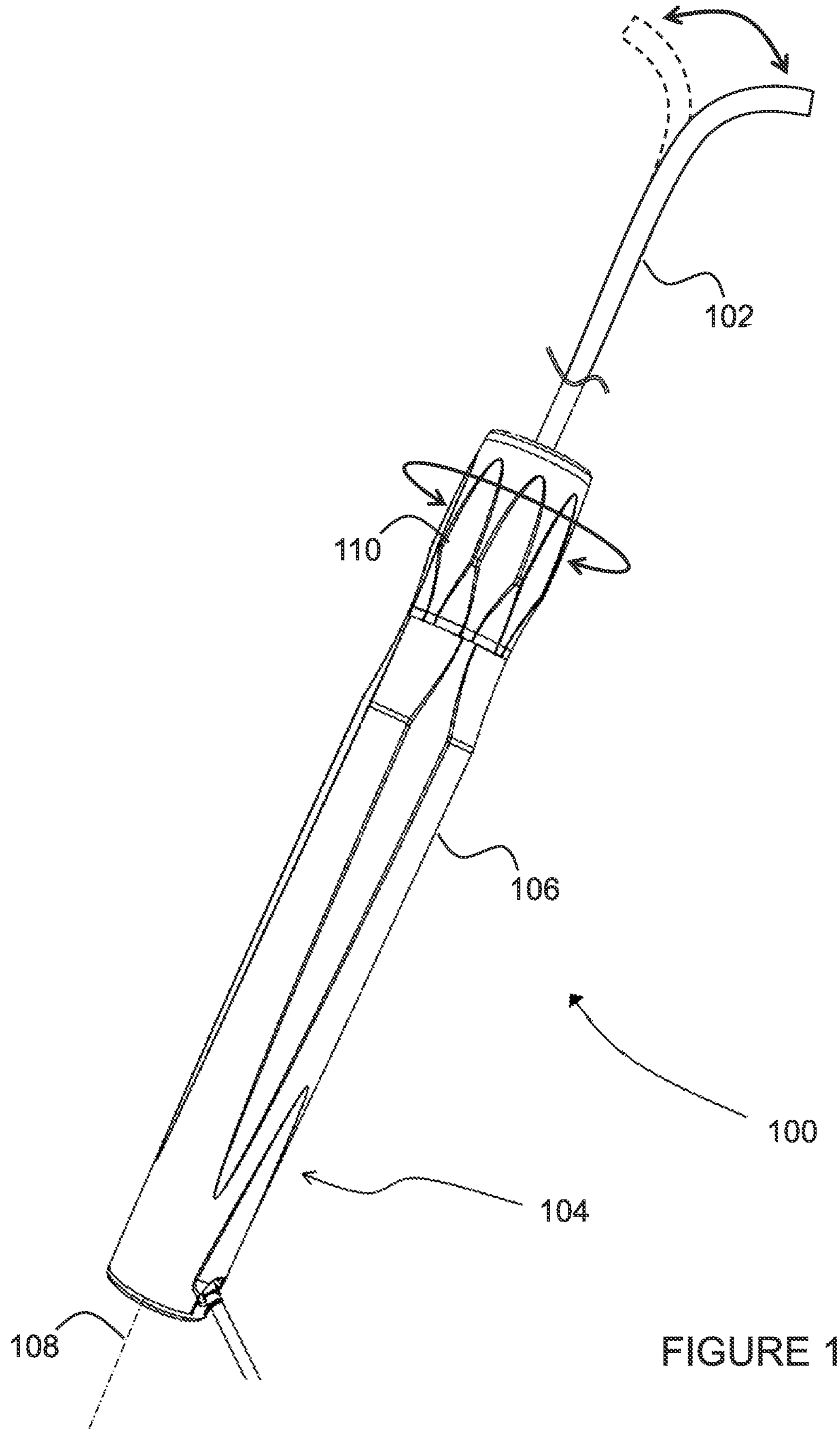
FIG. 1 is a perspective view of an example medical device.

Referring now to FIG. 1, an example steerable medical device 100 is shown. The steerable medical device 100 generally includes an elongate tool 102 and a handle 104 mounted to the tool for handling and manipulating the tool 102. The tool 102 can be, for example (but not limited to), a sheath, a catheter, or an introducer.

Referring still to FIG. 1, the handle 104 includes a handle body 106 (also referred to as a housing), which extends along a handle axis 108, and a knob 110 that is rotatable about the handle axis 108 with respect to the handle body 106. In alternative examples, the knob can be rotatable about a knob axis that is perpendicular to the handle axis, or at another non-parallel orientation with respect to the handle axis.

Referring still to FIG. 1, in the example shown, rotation of the knob 110 in a first rotational direction (e.g. clockwise) can cause the tool 102 to deflect in a first deflectional direction (i.e. to the configuration shown in solid line in FIG. 1), and rotation of the knob 110 in a second rotational direction (e.g. counter-clockwise) can cause the tool 102 to deflect in a second deflectional direction (i.e. to the configuration shown in dotted line in FIG. 1).

Figure 2:
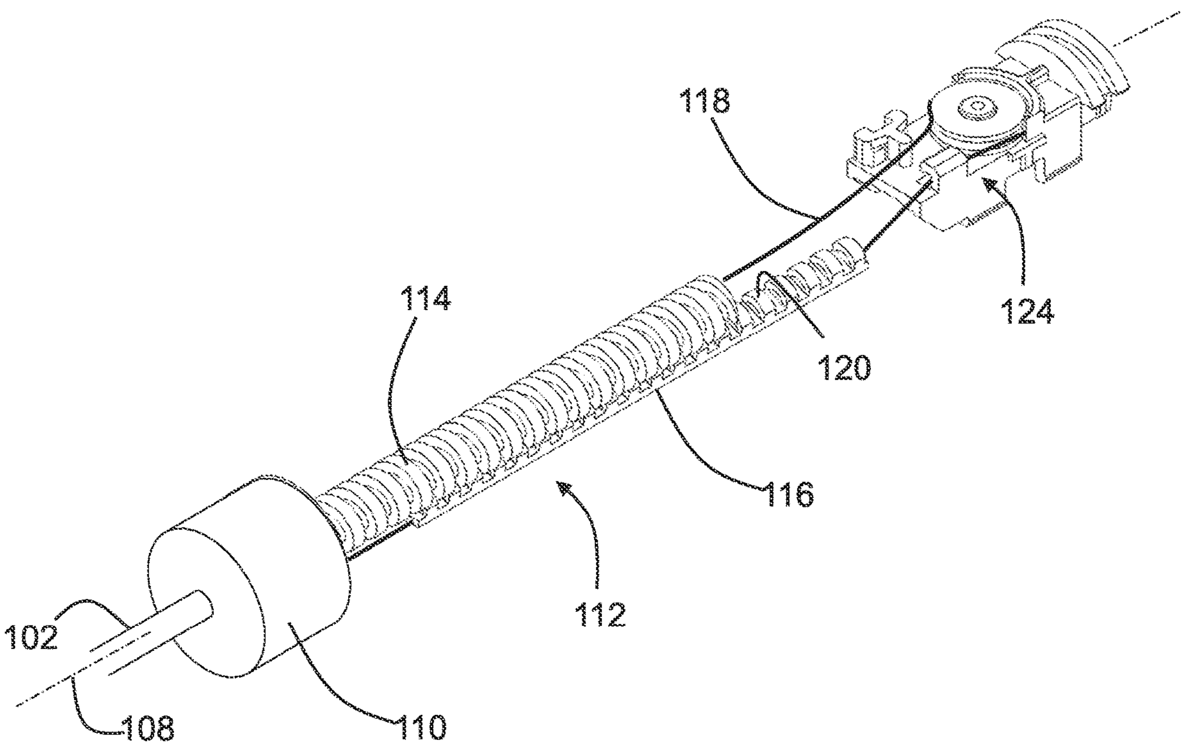
FIG. 2 is a perspective view showing the interior of the handle of the medical device of FIG. 1.

Referring to FIG. 2, in which the handle body 106 is omitted to show the interior thereof, a steering assembly 112 is provided for causing deflection of the tool 102 by rotation of the knob 110. In the example shown, the steering assembly 112 generally includes a first gear 114, a slider 116, and a control wire 118.

Referring still to FIG. 2, the first gear 114 is housed in the handle 104 (i.e. the first gear 114 can be fully housed in the handle body 106, or can be partially housed in the knob 110 and partially housed in the handle body 106) and is associated with the knob 110, so that rotation of the knob 110 drives rotation of the first gear 114. That is, rotation of the knob 110 is transmitted to the first gear 114. In the example shown, the first gear 114 is a worm screw that is rotatable about the handle axis 108 by rotation of the knob 110. For example, the worm screw can be fixed to the knob 110, or can be coupled to the knob 110 by at least one additional gear (e.g. the knob can include an internal gear, a sun gear can be fixed to the worm screw, and a planetary gear can be positioned between the internal gear and the sun gear; not shown).

Figure 3:
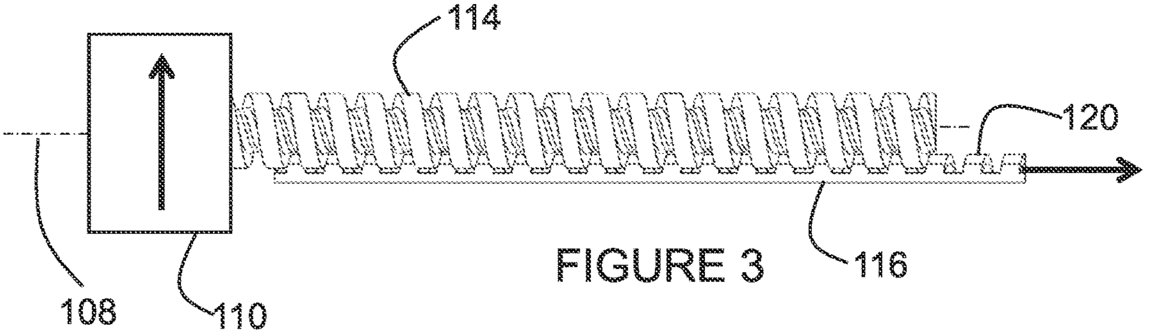
FIG. 3 is side view of the knob, first gear, and slider of the handle of FIG. 2, in a first position.
Figure 4:
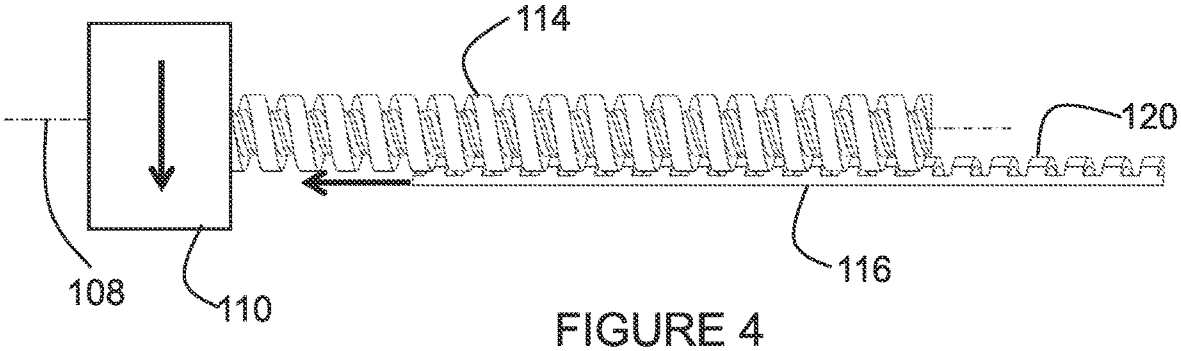
FIG. 4 is side view of the knob, first gear, and slider of the handle of FIG. 2, in a second position.

Referring still to FIG. 2, and also to FIGS. 3 and 4, the slider 116 is housed within the handle body 106, and includes a rack 120 that is engaged with the first gear 114, so that rotation of the first gear 114 drives translation of the slider 116 with respect to the handle body 106. The slider 116 is translatable within the handle body 106 (not shown in FIGS. 3 and 4), along the handle axis 108. That is, as shown in FIGS. 3 and 4, the slider 116 is translatable proximally (i.e. away from the tool 102, not shown in FIGS. 3 and 4) by rotation of the first gear 114 in a first direction, and is translatable distally (i.e. towards the tool 102) by rotation of the first gear 114 in a second direction. The slider 116 can be mounted to a track (not shown), which can limit the movement of the slider 116 to translation along the handle axis 108, and prevent movement in other directions (e.g. prevents movement perpendicular to the handle axis 108).

Referring back to FIG. 2, the control wire 118 is coupled between the slider 116 and the tool 102, via a control wire carriage assembly 124. Translation of the slider 116 causes tensioning of the control wire 118, and tensioning of the control wire 118 causes deflection of the tool 102 (as noted above, the control wire 118 and the connection between the control wire 118, the tool 102, and the slider 116 are shown schematically in the Figures, and the details thereof are not disclosed herein).

In an alternative example (not shown), rather than a worm gear, the steering assembly can include a pinion gear engaged with the rack. The pinion gear can be rotatable about an axis of rotation that is perpendicular to the handle axis, and one or more additional gears can be provided between the knob and the pinion gear (e.g. one or more bevel gears).

In any of the above examples, the steering assembly can include a pawl or latch or other component configured to prevent movement of the slider when the control wire is under tension.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

I claim:

1. A steerable medical device comprising:

an elongate tool;

a handle mounted to the tool and having a handle body and a knob that is rotatable with respect to the handle body;

a first gear housed within the handle and associated with the knob, whereby rotation of the knob drives rotation of the first gear, wherein the first gear is a worm screw, a slider housed within the handle body and including a rack engaged with the first gear, wherein the rack comprises a plurality of teeth having convex tip surfaces, whereby rotation of the first gear drives translation of the slider with respect to the handle body; and at least one control wire coupled to the slider and to the tool, whereby translation of the slider causes tensioning of the control wire, and tensioning of the control wire causes deflection of the tool.

2. The steerable medical device of claim 1, wherein the handle extends along a handle axis, and the slider is translatable along the handle axis.

3. The steerable medical device of claim 2, wherein the knob is rotatable about the handle axis, and the first gear is rotatable about the handle axis.

4. The steerable medical device of claim 1, wherein the tool is a sheath, a catheter, or an introducer.

5. A handle for a steerable medical device, the handle comprising:

a handle body and a knob that is rotatable with respect to the handle body;

a first gear housed within the handle and associated with the knob, whereby rotation of the knob drives rotation of the first gear, wherein the first gear is a worm screw;

a slider housed within the handle body and including a rack engaged with the first gear, wherein the rack comprises a plurality of teeth having convex tip surfaces, whereby rotation of the first gear drives translation of the slider with respect to the handle body; and at least one control wire coupled to the slider, whereby translation of the slider causes tensioning of the control wire.

6. The handle of claim 5, wherein the handle extends along a handle axis, and the slider is translatable along the handle axis.

7. The handle of claim 6, wherein the knob is rotatable about the handle axis, and the first gear is rotatable about the handle axis.

8. A method for operating a medical device, the method comprising:

rotating a knob of a handle;

transmitting rotation of the knob to a first gear associated with the knob, wherein the first gear is a worm screw;

engaging the first gear with a rack of a slider comprising a plurality of teeth having convex tip surfaces to cause translation of the slider by rotation of the first gear;

causing tensioning of a control wire by translation of the slider; and causing deflection of a tool by tensioning of the control wire.

9. The method of claim 8, wherein step a. comprises rotating the knob about a handle axis, and step b. comprises rotating the first gear about the handle axis.

* * * * *